US009375191B2

(12) United States Patent
Verstraelen et al.

(10) Patent No.: US 9,375,191 B2
(45) Date of Patent: Jun. 28, 2016

(54) METHOD AND APPARATUS FOR DETERMINING THREE-DIMENSIONAL RECONSTRUCTION OF AN OBJECT

(75) Inventors: Boudewijn J. A. Verstraelen, Lanaken (BE); Jean-Paul Aben, Limbricht (NL); Rianne Reinartz, Neerbeek (NL)

(73) Assignee: Pie Medical Imaging B.V., Maastricht (NL)

( * ) Notice: Subject to any disclaimer, the term of this patent is extended or adjusted under 35 U.S.C. 154(b) by 271 days.

(21) Appl. No.: 13/609,357

(22) Filed: Sep. 11, 2012

(65) Prior Publication Data

US 2013/0064343 A1 Mar. 14, 2013

(30) Foreign Application Priority Data

Sep. 13, 2011 (EP) ..................................... 11181152

(51) Int. Cl.
*A61B 6/00* (2006.01)
*G06T 11/00* (2006.01)

(52) U.S. Cl.
CPC ................ *A61B 6/504* (2013.01); *A61B 6/466* (2013.01); *A61B 6/469* (2013.01); *G06T 11/006* (2013.01)

(58) Field of Classification Search
CPC ............ A61B 6/02; A61B 6/022; A61B 6/03; A61B 6/032; A61B 6/504; A61B 6/5211; A61B 6/5223; A61B 6/4429; A61B 6/4435; A61B 6/4441; A61B 6/503; A61B 6/5205
USPC ............... 378/4, 15, 20, 21, 25; 382/128, 130
See application file for complete search history.

(56) References Cited

U.S. PATENT DOCUMENTS

| 6,980,690 | B1 | 12/2005 | Taylor et al. | |
| 2003/0078500 | A1* | 4/2003 | Evron | A61B 6/504 600/443 |
| 2004/0019264 | A1 | 1/2004 | Suurmond et al. | |
| 2005/0203381 | A1* | 9/2005 | Harder | G01R 33/563 600/420 |

(Continued)

FOREIGN PATENT DOCUMENTS

| EP | 1280459 B1 | 5/2008 |
| WO | WO2012028190 A1 | 3/2012 |

OTHER PUBLICATIONS

"3D Heart-Vessel Reconstruction from Biplane Angiograms" Whale et al. IEEE Computer Graphics and Applications, vol. 16, No. 1, Jan. 1996 pp. 65-73.

(Continued)

*Primary Examiner* — Robert Kim
*Assistant Examiner* — David E Smith
(74) *Attorney, Agent, or Firm* — Gordon & Jacobson, P.C.

(57) ABSTRACT

A computer-implemented method for determining a 3D surface reconstruction of an object, which comprises generating a first 3D surface reconstruction of the object from a plurality of 2D images of the object obtained from different perspectives. A region of interest of the object is specified. At least one viewing direction is determined for viewing the specified region of interest. At least one 2D image of the object corresponding to the at least one viewing direction is obtained. A second 3D surface reconstruction of the object is generated from all or part of the 2D images used to generate the first 3D surface reconstruction and the at least one 2D image of the object corresponding to the at least one viewing direction for the specified region of interest. A corresponding apparatus and computer program are also disclosed.

20 Claims, 3 Drawing Sheets

(56) References Cited

U.S. PATENT DOCUMENTS

| | | | | |
|---|---|---|---|---|
| 2007/0025508 | A1* | 2/2007 | Ohishi | A61B 6/4441 378/62 |
| 2008/0095423 | A1* | 4/2008 | Redel | A61B 6/481 382/131 |
| 2009/0060298 | A1* | 3/2009 | Weijers | G06T 7/0012 382/128 |
| 2009/0087068 | A1* | 4/2009 | Sakaguchi | A61B 6/12 382/132 |
| 2009/0297005 | A1* | 12/2009 | Heigl | A61B 6/032 382/130 |
| 2010/0014740 | A1* | 1/2010 | Movassaghi | A61B 6/4441 382/132 |
| 2010/0021025 | A1* | 1/2010 | Hof | G06T 7/0012 382/128 |
| 2011/0153254 | A1* | 6/2011 | Hartov | A61B 5/06 702/103 |

OTHER PUBLICATIONS

"A Novel Dedicated 3-Dimensional Quantitative Coronary Analysis Methodology for Bifurcation Lesions", Onuma et al, EuroIntervention 2011; 6:1-00.

"Segmentation of Coronary Vessel Structures in X-ray Angiogram Images by Using Spatial Pattern Matching Method", C. Kose et. al., IEEE 23rd International Symposium on Computer and Information Sciences, 2008, ISCIS '08 pp. 1-6.

"The Singular Value Decomposition: Its Computation and Some Applications", V. Klema et. al, IEEE Transactions on Automatic Control, 1980, vol. 25, Issue 2, pp. 164-176.

"Computer Assisted Coronary Intervention by Use of On-Line 3D Reconstruction and Optimal View Strategy", Chen et al, Medical Image Computing and Computer-Assisted Intervention, MICCAI International Conference Proceedings, Oct. 11, 1998, pp. 377-385.

* cited by examiner

METHOD AND APPARATUS FOR DETERMINING THREE-DIMENSIONAL RECONSTRUCTION OF AN OBJECT

CROSS-REFERENCE TO RELATED APPLICATIONS

The present application claims priority from EP Patent Appl. No. EP11181152.7, filed on Sep. 13, 2011, herein incorporated by reference in its entirety.

BACKGROUND

1. Field

The present application relates to a method and apparatus for determining optimal 3D reconstruction of an object of interest, particularly from angiographic projections.

2. State of the Art

Angiography is a commonly used imaging modality within a numerous variety of interventions. During such interventions it is very important that the clinician gets a good understanding of the object in question. For example in vascular interventions it is important that the clinician has all information concerning the part of the vessel tree of interest. This is necessary when, for instance, a stent is to be placed in a bifurcated vessel, where a bifurcated vessel is a main artery or vein that has split up into two or more further arteries or veins.

Two-dimensional (2D) angiographic imaging, such as X-ray, frequently lacks the possibility to visualize the bifurcation region correctly. Specifically, the carina position of the bifurcation, which is defined as the point where the vessel splits, is a challenge to visualize correctly with 2D angiographic imaging because of overlap of one or more of the vessel segments connected to the bifurcation.

If not all information about this bifurcated tubular shaped object is known by the physician, this can have severe consequences. For instance, an obstruction at the bifurcation can be missed or underestimated or the wrong stent dimension can be selected. This can lead to serious complications for the patient. Furthermore, in addition to the one-stent approach, new bifurcation stenting techniques, such as two-stent approaches and even use of dedicated bifurcation stents, are more and more used during cardiovascular interventional treatment of bifurcated vessels. These new treatment techniques require accurate information of the tubular shaped object in question. A way to acquire such information of the object under examination is through high resolution volumetric images acquired with CT or MR systems. These imaging acquisition systems need to have the patients, especially the part to be imaged, inside the apparatus and access for interventional treatment is cumbersome. Also these apparatus provide a great amount of image data, whose processing is time-consuming and makes it unrealistic to perform imaging sessions in real-time where the object of interest needs to be visualized in real time during the intervention.

In practice interventional treatment is generally performed under guidance of 2D images acquired with angiographic X-ray systems of the so-called C-arm or L-arm type. These systems allow acquisition of 2D images from different directions, also called 2D projections, of the object under examination. These different projections can be obtained by rotating the arm holding the X-ray source and the image intensifier around the patient.

A three-dimensional (3D) reconstruction from 2D images acquired in two different projections is possible however there remains some uncertainty also in the 3D reconstruction on the exact shape of the vessel around the bifurcation due to overlap in the 2D images used to reconstruct the bifurcated vessel in 3D space.

An example of the problems with overlap is visualized in FIG. 1. Only the last image shows the true shape of the bifurcation resulting in a proper visualization of the carina.

Of course one could try to find an optimal projection with trial and error, but the extended number of images obtained during the intervention increase the radiation dose, the amount of contrast fluids, and can significantly increase the procedure time, all of which may have a negative influence on the health of the patient.

Document EP1280459 discloses a method for helping the clinician to reduce the number of perspectives needed for a proper 3D reconstruction by using a 3D model for determining two 2D projections upon which a new 3D model is to be reconstructed in order to better represent the object of interest. This document, although going in the right direction, is, however, aimed at straight arterial segments and requires further exposure of the patient to obtain at least two new projections.

There's thus the need for a method to assist the clinician to analyze the details of the bifurcation with the number of images needed reduced to an absolute minimum while also obtaining the maximum amount of image information concerning the bifurcated tubular shaped object under study.

SUMMARY

It is thus an object of the present application to provide a method for determining a 3D reconstruction of an object (such as a bifurcated or splitting tubular object) from 2D images of the object with a reduced procedure time and imaging related load for the patient.

The present application reaches this aim with a method for determining a three-dimensional surface reconstruction of an object, the method comprising:
a) generating a first 3D surface reconstruction of the object from a plurality of two-dimensional (2D) images of the object which have been obtained from different perspectives;
b) specifying a region of interest of the object;
c) determining at least one viewing direction for viewing the region of interest of the object of b);
d) obtaining at least one 2D image of the object corresponding to the at least one viewing direction of c);
e) generating a second 3D surface reconstruction of the object from all or part of the 2D images used to generate the first 3D surface reconstruction of the object in a) and the at least one 2D image of the object obtained in d).

To restrain the dosage used for the patient, only one further 2D image can be used. Furthermore, as the region of interest can be varied, an optimal perspective can be determined taking also into account the complexity of the geometry of the object as, for example, in the case of n-furcated tubular vessels. In this manner it is ensured that no image information is lost and that all images have a maximum contribution for the end result with the minimum cost in term of patient exposure to radiation and contrast fluids.

For example, when an additional image that has a clear view on the carina of a bifurcation is added to the original images used for the 3D reconstruction uncertainty on the exact shape of the bifurcation is minimized.

This method makes it possible to select the proper projection to acquire such an additional image. Of course, if such an additional image has already been acquired, for example during a previous examination, there's no need to acquire a new image again. Such an already acquired image can be used for the purpose. This is the case, for example, of an image with the right perspective picked up from a collection of images that were obtained in an earlier stage. For this reason the term "obtaining a 2D image" has been used within the present description and the claims so as to include both alternatives, i.e. acquiring a new 2D image with the imaging device or selecting the 2D image from a storage device or medium.

Further, the methodology of the present application makes it possible to select an optimal image out of a set of images from different projections that are already available. These images may be acquired with a rotation around the bifurcated vessel either with a linear or a non-linear rotation movement of the X-ray gantry.

If the bifurcated vessel is very complex or is in fact a trifurcation or an N-furcation in general, addition of an additional image based on the calculation of a position perpendicular to two other legs of the bifurcation or three other legs in case of a trifurcation (N legs in the general case of an N-furcation) can further improve the accuracy of the 3D reconstruction and the analysis of the different dimensions of the vessels also near to their connection points.

Advantageously, the step of receiving from the user a section or area or volume of interest comprises receiving the area/region of interest in at least one of the 2D images used for the three-dimensional reconstruction of the object or in the 3D reconstruction itself. The determined perspective is considered optimal in terms of absence or at least reduction of obscured details for such section or area or volume of interest as seen above. Such perspective is preferably in a direction substantially perpendicular to a cut plane of the object, typically the plane containing the section of interest.

According to a preferred embodiment, the object is a tubular vessel or a tree of tubular vessels. In this case the section or area or volume of interest can advantageously comprise an N-furcation, particularly a bifurcation. An N-furcation is a part of the vessel or the tree where a proximal tubular organ branches into N distal tubular organs with N>2. In this case, the new perspective can be determined as a direction substantially perpendicular to a plane fitting all the branches of the N-furcation.

Preferably the object or a part thereof is segmented in at least two of the 2D images used for the 3D surface reconstruction of the object. The region of interest can manually or automatically be identified on the 2D images used for the 3D surface reconstruction of the object or directly located on the 3D reconstruction of the object.

According to an embodiment, the plurality of 2D images are angiographic images showing a bifurcation.

In general all the steps of the method of the present application are not to be considered strictly in the order presented, but can be equally performed in any other meaningful sequence. For example, the step of determination of the region of interest within the 3D surface reconstruction can be simply omitted. In this case, the whole 3D surface reconstruction can be considered for further processing and a perspective can be determined that add information on missing details due to overlap or other obscuring factors in the originally used 2D images.

The method of the present application is typically performed by a data processing system with access to 2D images of an object of interest obtained from different perspectives.

According to an improvement, it is possible to provide quantitative analysis of a tree or part of a tree of recursively splitting tubular organs starting from the 3D surface reconstruction of such a tree or part of a tree with, for example, the following additional steps:

defining the 3D centerlines of said tree or part of the tree;
identifying the branches of the tree;
identifying N-furcations of the tree or part of the tree, an N-furcation being a part of the tree where a proximal tubular organ branches into N distal tubular organs with N 2,
dividing each branch in one or more regions, such regions being of two different types, named single vessel region and splitting region, different cross-section surfaces being defined in such regions, wherein said splitting regions can exist at the proximal side of a branch as well as at the distal side of said branch, and each N-furcation comprises the distal splitting region of a branch and the proximal splitting regions of the N branches directly distal to said branch.

The application also relates to a computer product directly loadable into the memory of a computer and comprising software code portions for performing the method as disclosed above when the product is run on a computer.

According to another aspect, the present application also relates to an apparatus for processing 2D projection images of a 3D object for performing the method as disclosed above. The apparatus comprises means for optionally receiving, from a user, indications on the position of a region of interest in at least two 2D images of the object obtained from different perspectives or in the 3D surface reconstruction of the object and processing means programmed for performing the method according to the present application to determine a 3D surface reconstruction of the object.

Advantageously, such an apparatus could be the same machine used for acquiring and/or reconstructing the image data, such as Ultrasound or X-ray machines. Particularly it is an angiographic apparatus of the C-arm or L-arm type with X-ray source and image intensifier respectively located at opposite sides of the arm, such arm being movable at least according to a rotation angle and an angulation angle with reference to a patient to obtain 2D images from different perspectives, the processing means being programmed to calculate rotation and angulation angles of the arm for obtaining an optimal projection image to be used for updating the 3D reconstruction.

According to an embodiment, the angiographic apparatus comprises actuating means to automatically or semi-automatically rotate the arm, and/or display means for providing to a user indications for manually rotating the arm, according to rotation and angulation angles calculated for obtaining an optimal projection image.

The processing means could be a processor or processors dedicated to perform the method according to the present application or, in a particularly advantageous configuration, the same, or part of the same, processing means that subtends the main image acquisition functionalities of the machine thus obtaining a very compact and powerful apparatus.

BRIEF DESCRIPTION OF THE DRAWINGS

The characteristics of the invention and the advantages derived therefrom will be more apparent from the following description of non-limiting embodiments, illustrated in the annexed drawings.

DETAILED DESCRIPTION OF THE PREFERRED EMBODIMENTS

Figure 1:
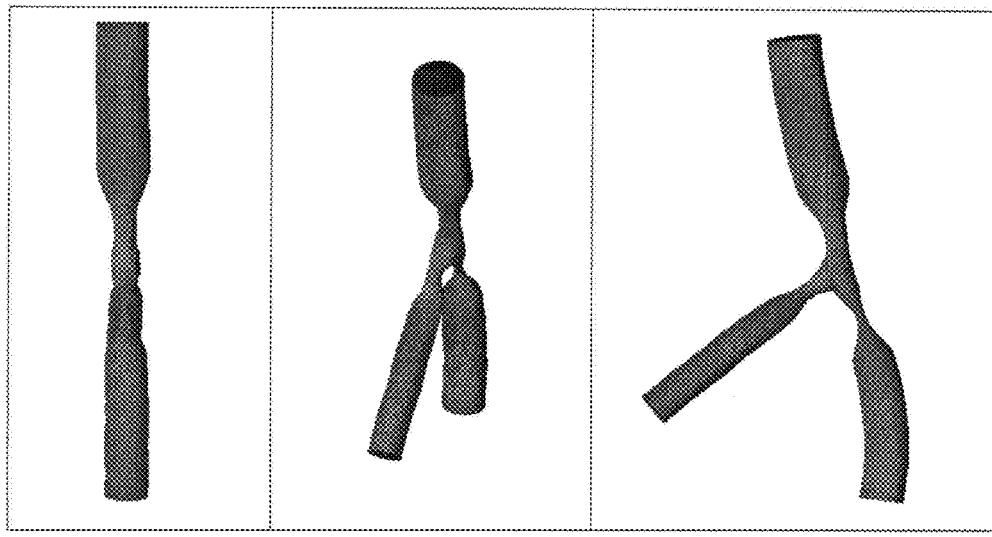
FIG. 1 shows a bifurcated tubular shaped object from different perspectives.
Figure 2:
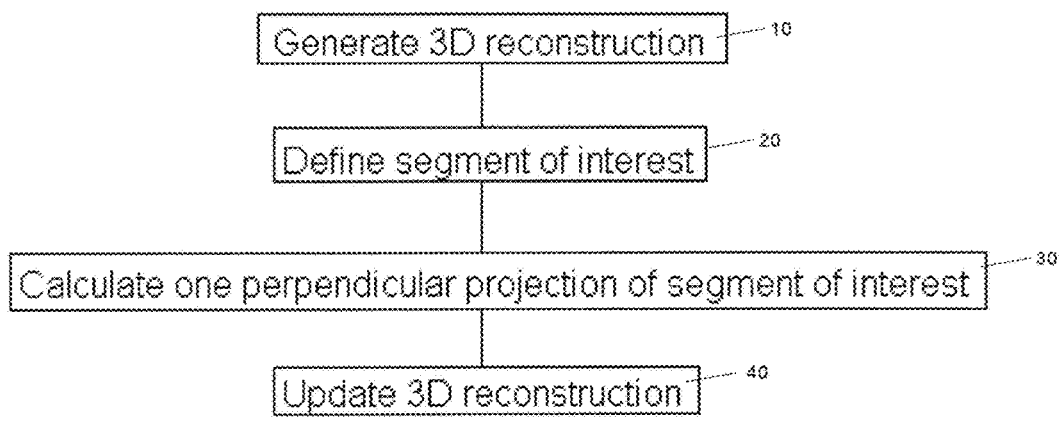
FIG. 2 is a flowchart of an exemplary method for determining a three-dimensional surface reconstruction of an object.

With reference to the block diagram of FIG. 2, an embodiment of a method for determining a three-dimensional surface reconstruction of an object is now described.

In this example it is assumed to have at disposal at least two projection images of an object of interest, particularly a tubular shaped object such as an artery or vein bifurcation. Any image device capable of providing 2D images can be used for the purpose. For example, a bi-plane or single plane angiographic system can be used such as those manufactured, for example, by Siemens (Artis zee Biplane) or Philips (Allura Xper FD).

In the step indicated with reference number 10 a three-dimensional reconstruction (also called 3D model or three-dimensional surface reconstruction within the present disclosure) of the object of interest is made using two two-dimensional angiographic images. This is done made for example employing the methodology described in Whale, Oswald, Fleck, "3D Heart-Vessel reconstruction from biplane angiograms", IEEE Computer Graphics And Applications Vol. 16, No. 1, January 1996 pp. 65-73 or "A novel dedicated 3-dimensional quantitative coronary analysis methodology for bifurcation lesions", Yoshinobu Onuma, Chrysafios Girasis, Jean-Paul Aben, Giovanna Sarno, Nicolo Piazza, Coen Lokkerbol, Marie-Angel Morel, Patrick W. Serruys, EuroIntervention 2011; 6:1-00.

Reconstruction step 10 may be preceded by a segmentation step not shown in the figure. This can be done according to any known method such as in C. Kose et. al. "Segmentation of coronary vessel structures in X-ray angiogram images by using spatial pattern matching method" IEEE 23rd International Symposium on Computer and Information Sciences, 2008, ISCIS '08 pages 1-6.

Figure 3:
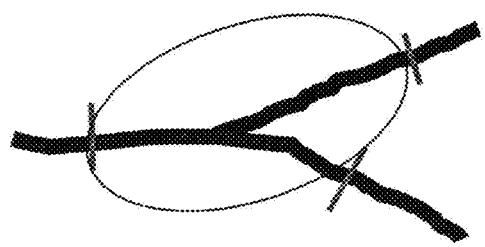
FIG. 3 shows a 2D image of a bifurcation with an ellipse superimposed to define a section of interest.

Because the user is usually interested in a smaller section of the generated 3D model, in the previously generated 3D reconstruction a segment of interest can be indicated (step 20). This can be done, for instance, by indicating two lines in one of the 2D images, one representing the beginning and the other representing the end of the wanted segment. In case of an N-furcation N lines can be used, one for each branch of the N-furcation. Also a circle, an ellipse or any other geometrical figure can be used for indicating the section or sub-region of interest as shown, for example, in FIG. 3. Of course the selection of the segment of interest can be done also directly on the 3D model.

Figure 4:
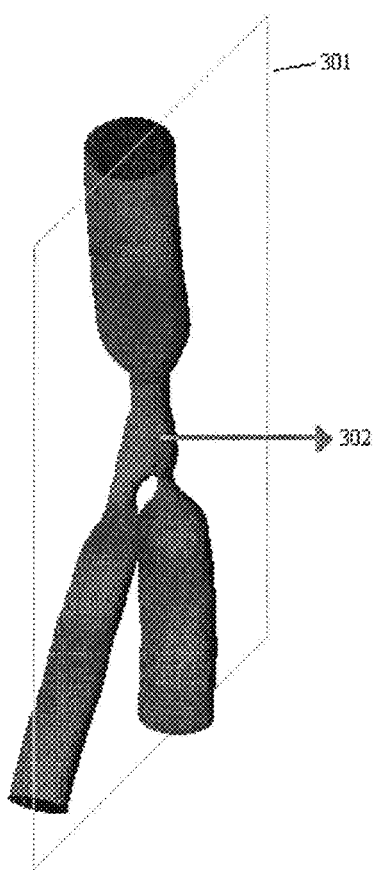
FIG. 4 is a simplified sketch showing the plane to be used as the optimal projection in case of a bifurcated tubular shaped object.

Once the segment of interest is identified, a projection is determined that is perpendicular to the main direction of the segment of interest (step 30). This perpendicular projection is determined by fitting one plane through all different branches of the bifurcation as obtained from the 3D reconstruction. The fitting process is done, for example, by using singular value decomposition as taught by V. Klema et. al "The singular value decomposition: Its computation and some applications" IEEE Transactions on Automatic Control, 1980, Volume 25, Issue 2, pages 164-176. The matrix D on which the singular value decomposition is used is composed using each different bifurcation branch per row. The result of the singular value decomposition is in the form of three matrices following $D = U*W*V_T$. Each row of V holds a quad-tuple $\{a,b,c,d\}$ that defines a plane following $ax+by+cz+d=0$. The requested plane (denoted as 301 in FIG. 4) is the plane that corresponds to the row j of V for which W(j,j) is minimal.

The optimal perspective is then defined as the view that is perpendicular to this plane. This view is given by $\{a,b,c\}$ of row j of V and is equal to the normal of the plane (denoted as 302 in FIG. 4).

The physician can then acquire a 2D angiographic image from this perspective (unless he already has at his disposal such an image for example in a storage device). Using this new image, either acquired or picked up from a stored collection, the already made 3D model (step 10) is improved with the gathered image information (step 40). This is done by rebuilding the 3D model this time based on three 2D images using same or similar techniques as seen above for step 10. This updated 3D model now holds the maximum amount of object information with the least amount of time and burden to the patient spent on finding that information.

Once the new 3D model is available, this can be used for computing geometric parameters, such as, in the case of a bifurcation, a bifurcation angle, obstruction extent, obstruction amount, obstruction length, etc. by using, for example, the teachings of US Patent Application No. 20100021025, filed on Jul. 22, 2008 or PCT Application No. EP/2010/062883, filed on Sep. 2, 2010, both commonly assigned to assignee of the present application and herein incorporated by reference in their entireties.

Figure 5:
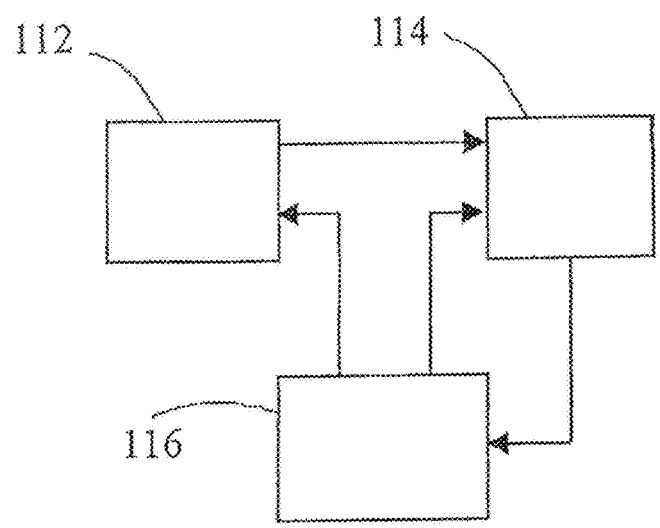
FIG. 5 is a functional block diagram of an exemplary bi-plane angiographic system.

FIG. 5 is a functional block diagram of an exemplary bi-plane angiographic system, which includes a bi-plane angiographic imaging apparatus 112 that operates under commands from user interface module 116 and will provide data to data processing module 114. The bi-plane angiographic imaging apparatus 112 captures two-dimensional X-ray images of the vessel organ of interest for example in the postero-anterior (PA) direction and in the lateral direction (which is substantially orthogonal to the PA direction). The bi-plane angiographic imaging apparatus 112 typically includes a first X-ray source and detector pair mounted on one arm of a supporting gantry as well as a second X-ray source and detector pair mounted on second arm of the supporting gantry. The gantry provides for positioning the arms of the first and second X-ray source and detector pairs at various angles with respect to a patient who is supported on a table between the X-ray source and detector of the respective pair. The data processing module 114 may be realized by a personal computer, workstation or other computer processing system. The data processing module 114 processes the two-dimensional images captured by the bi-plane angiographic imaging apparatus 112 to generate data as described herein. The user interface module 116 interacts with the user and communicates with the data processing module 114. The user interface module 116 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 114 and the user interface module 116 cooperate to carry out the operations of FIG. 2 as described herein.

The operations of FIG. 2 can also be carried out by software code that is embodied in a computer product (for example, an optical disc or other form of persistent memory such as a USB drive or a network server). The software code can be directly loadable into the memory of a data processing system for carrying out the operations of FIG. 2 as described herein.

In this example it is assumed that the imaging system has acquired and stored at least two two-dimensional images of an object of interest.

There have been described and illustrated herein several embodiments of a method (and corresponding program storage device, data processing system, and imaging apparatus) for determining a three-dimensional surface reconstruction of an object. While particular embodiments have been described, it is not intended that the present application be limited thereto, as it is intended that the present application be as broad in scope as the art will allow and that the specification be read likewise. It will therefore be appreciated by those skilled in the art that yet other modifications could be made to the system, methodology, apparatus and devices of the present application without deviating from its spirit and scope as claimed.

What is claimed is:

1. A computer-implemented method for determining a three-dimensional (3D) surface reconstruction of at least one tubular vessel, the method comprising:
   a) generating a first 3D surface reconstruction of the at least one tubular vessel from a set of two-dimensional (2D) angiographic X-ray images of the at least one tubular vessel which have been obtained from different perspectives;
   b) specifying an N-furcation of the at least one tubular vessel where a proximal tubular organ branch splits into N distal tubular organ branches, wherein N is an integer greater than or equal to 2;
   c) determining at least one viewing direction for viewing the N-furcation of the at least one tubular vessel of b), wherein the at least one viewing direction is substantially perpendicular to a plane that extends through the proximal and distal tubular organ branches of the N-furcation of b);
   d) obtaining at least one 2D angiographic X-ray image of the at least one tubular vessel corresponding to the at least one viewing direction of c); and
   e) updating the first 3D surface reconstruction of the at least one tubular vessel by generating a second 3D surface reconstruction of the at least one tubular vessel from all or part of the set of 2D angiographic X-ray images used to generate the first 3D surface reconstruction of the at least one tubular vessel in a) and the at least one 2D angiographic X-ray image of the at least one tubular vessel obtained in d).

2. A computer-implement method according to claim 1, wherein:
   the N-furcation of the at least one tubular vessel of b) pertains to at least one 2D angiographic X-ray image of the at least one tubular vessel used to generate the 3D surface reconstruction of the at least one tubular vessel in a).

3. A computer-implemented method according to claim 1, wherein:
   the N-furcation of the at least one tubular vessel of b) pertains to the 3D surface reconstruction of the at least one tubular vessel generated in a).

4. A computer-implemented method according to claim 1, wherein:
   the N-furcation of the at least one tubular vessel of b) is specified by a user.

5. A computer-implemented method according to claim 1, wherein:
   the N-furcation of the at least one tubular vessel of b) is specified automatically.

6. A computer-implemented method according to claim 1, wherein:
   the at least one viewing direction provides a view of details of the N-furcation of the at least one tubular vessel of b) that were obscured in the 2D angiographic X-ray images used for the 3D reconstruction of the at least one tubular vessel in a).

7. A computer-implemented method according to claim 6, wherein:
   the at least one viewing direction is optimal in terms of reduction of obscured details for the N-furcation of the at least one tubular vessel of b) in the 2D angiographic X-ray images used for the 3D reconstruction of the at least one tubular vessel in a).

8. A computer-implement method according to claim 1, wherein:
   the plane that extends through the proximal and distal tubular organ branches of the N-furcation is determined by fitting a plane through all of the proximal and distal tubular organ branches of the N-furcation using singular value decomposition.

9. A computer-implemented method according to claim 1, further comprising:
   prior to a), segmenting the at least one tubular vessel or part thereof in at least two of the 2D angiographic X-ray images used in the 3D surface reconstruction of b).

10. A computer-implemented method according to claim 1, wherein:
    the set of 2D angiographic X-ray images of a) are angiographic images showing part or the whole of the at least one tubular vessel.

11. A computer-implement method according to claim 1, wherein:
    the second 3D surface reconstruction of the at least one tubular vessel of e) provides a representation of the surface of the lumen wall of the tubular organs forming the at least one tubular vessel.

12. A computer-implemented method according to claim 11, further comprising:
    f) performing quantitative analysis of the surface of the lumen wall of the tubular organs forming the at least one tubular vessel.

13. A computer-implemented method according to claim 12, wherein:
    the quantitative analysis of f) involves
    i) defining 3D centerlines of the at least one tubular vessel;
    ii) identifying branches of the at least one tubular vessel;
    iii) identifying the N-furcations of the at least one tubular vessel; and
    iv) dividing the tubular organ branches of the N-furcations in one or more regions, such regions being of two different types including a single vessel region type and a splitting region type, wherein different cross-section surfaces are defined for types, wherein said splitting region type exists at the proximal side of a given tubular organ branch as well as at a distal side of the given tubular organ branch, and wherein each N-furcation includes the distal splitting region of a particular tubular organ branch and the proximal splitting regions of the N branches directly distal to the particular tubular organ branch.

14. A computer product directly loadable into the memory of a digital computer system and comprising software code portions embodying the computer-implemented method for determining a three-dimensional (3D) surface reconstruction of at least one tubular vessel according to claim 1.

15. An apparatus for acquiring two-dimensional (2D) projection images of a three-dimensional object, the apparatus comprising a data processing system programmed for performing the computer-implemented method for determining a three-dimensional (3D) surface reconstruction of at least one tubular vessel according to claim 1.

16. An apparatus according to claim 15, wherein:
the apparatus is an angiographic apparatus of the C-arm or L-arm type with an X-ray source and image intensifier respectively located at opposite sides of the arm, such arm being movable at least according to a rotation angle and an angulation angle with reference to a patient to obtain 2D images from different perspectives, the processing means being programmed to calculate rotation and angulation angles of the arm for obtaining optimal projection images.

17. An apparatus according to claim 16, further comprising:
an actuator configured to automatically or semi-automatically rotate the arm; and/or
a display configured to provide a user indications for manually rotating the arm, according to rotation and angulation angles calculated for obtaining an optimal projection image.

18. A computer-implemented method according to claim 1, wherein:
the at least one tubular vessel comprises a tubular vessel or a tree of tubular vessels.

19. A computer-implemented method for determining a three-dimensional (3D) surface reconstruction of at least one tubular vessel, the method comprising:

a) generating a first 3D surface reconstruction of the at least one tubular vessel from a set of two-dimensional (2D) angiographic X-ray images of the at least one tubular vessel which have been obtained from different perspectives;
b) specifying an N-furcation of the at least one tubular vessel where a proximal tubular organ branch splits into N distal tubular organ branches, wherein N is an integer greater than or equal to 2;
c) determining a single viewing direction for viewing the N-furcation of the at least one tubular vessel of b), wherein the single viewing direction is substantially perpendicular to a plane that extends through the proximal and distal tubular organ branches of the N-furcation of b);
d) obtaining a single 2D angiographic X-ray image of the at least one tubular vessel corresponding to the single viewing direction of c); and
e) updating the first 3D surface reconstruction of the at least one tubular vessel by generating a second 3D surface reconstruction of the at least one tubular vessel from all or part of the set of 2D angiographic X-ray images used to generate the first 3D surface reconstruction of the at least one tubular vessel in a) and the single 2D angiographic X-ray image of the at least one tubular vessel obtained in d).

20. A computer-implemented method according to claim 19, wherein:
the at least one tubular vessel comprises a tubular vessel or a tree of tubular vessels.

* * * * *